United States Patent [19]

Harvey

[11] Patent Number: 4,722,327

[45] Date of Patent: Feb. 2, 1988

[54] THERAPEUTIC APPARATUS

[76] Inventor: William J. Harvey, 5147 E. Enid Cir., Mesa, Ariz. 85206

[21] Appl. No.: 49,407

[22] Filed: May 14, 1987

[51] Int. Cl.[4] .......................... A61F 5/00; A61H 21/00

[52] U.S. Cl. ........................................ 128/44; 74/104; 104/53; 128/79; 272/141

[58] Field of Search ........................ 128/79, 33, 51, 52, 128/53, 44; 104/DIG. 1, 53; 254/84; 74/55, 104; 272/73, 141

[56] References Cited

U.S. PATENT DOCUMENTS

| | | | |
|---|---|---|---|
| 416,990 | 12/1889 | Campbell | 254/84 |
| 880,254 | 2/1908 | VanAntwerp | 104/53 |
| 2,052,447 | 8/1936 | Coderre | 104/DIG. 1 |
| 2,157,395 | 5/1939 | Benson | 128/52 |
| 3,504,665 | 4/1970 | Bakunin | 128/52 |
| 3,583,322 | 6/1971 | Vykukul | 104/307 |
| 3,724,451 | 4/1973 | Santo | 128/52 |
| 3,910,262 | 10/1975 | Stoughton | 128/79 |
| 4,531,459 | 7/1985 | Yamada | 104/53 |

FOREIGN PATENT DOCUMENTS

| | | | |
|---|---|---|---|
| 115794 | 12/1900 | Fed. Rep. of Germany | 128/33 |
| 275485 | 6/1914 | Fed. Rep. of Germany | 104/53 |
| 117957 | 1/1947 | Sweden | 254/8 B |

*Primary Examiner*—Clyde I. Coughenour
*Attorney, Agent, or Firm*—Charles P. Padgett, Jr.

[57] ABSTRACT

A therapeutic apparatus for relieving sexual frustrations in women without sex partners which includes a generally rectangular, substantially flat, platform with a pair of longitudinal rails mounted along the axis of the platform. A housing includes a lower flange for being operatively received within continuous slots formed at the lateral interior of the rails for constraining the movement of the housing to back and forth reciprocal motion between the tracks. An assembly is mounted to the front of the housing which includes an elongated, generally cylindrical artificial penis for simulating the look and feel of an erect human male's penis and an annular pad of relatively soft material disposed adjacent the front of the housing and about the base of the artificial penis for simulating the look and feel of a male's pubic hair. A rod is provided with a handle at one end so that the user, once the platform is disposed between the user's spread legs and thighs with the front end immediately adjacent her vulva, can reciprocally move the housing and the artificial penis attached thereto into and out of her vagina until she receives sexual gratification, preferably in the form of an orgasm.

20 Claims, 9 Drawing Figures

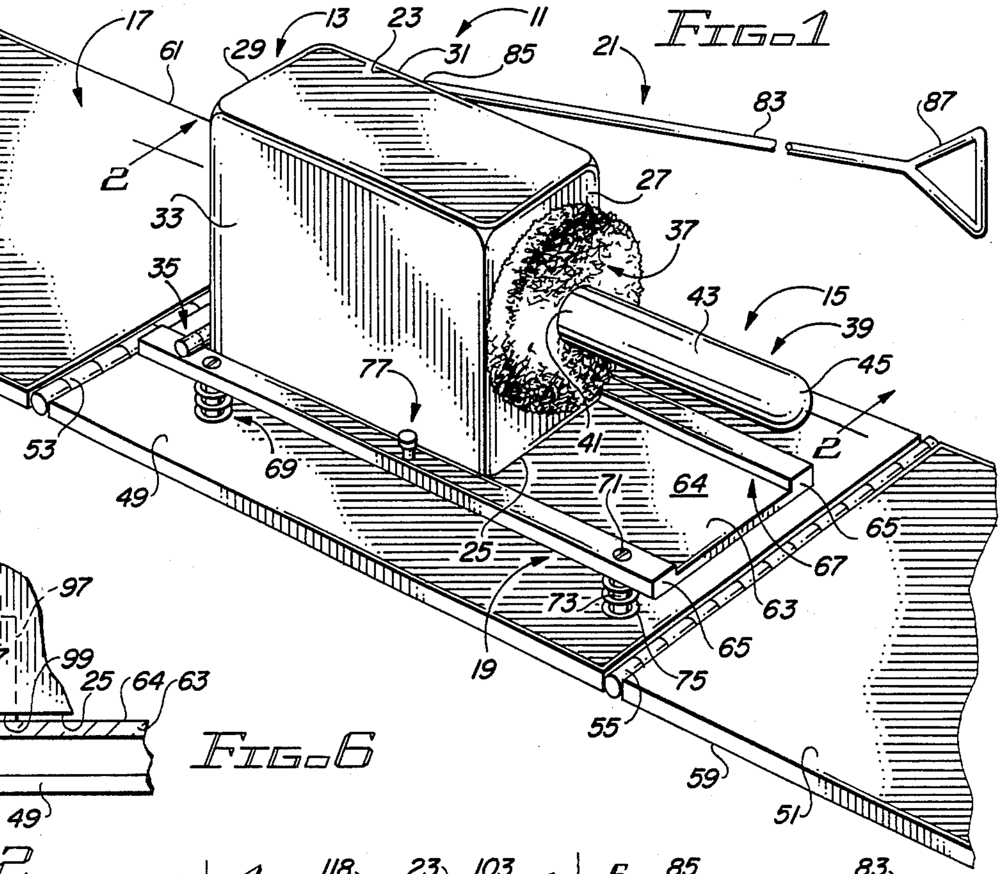
FIG. 1
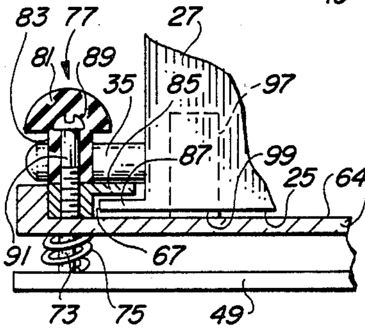
FIG. 6
FIG. 2
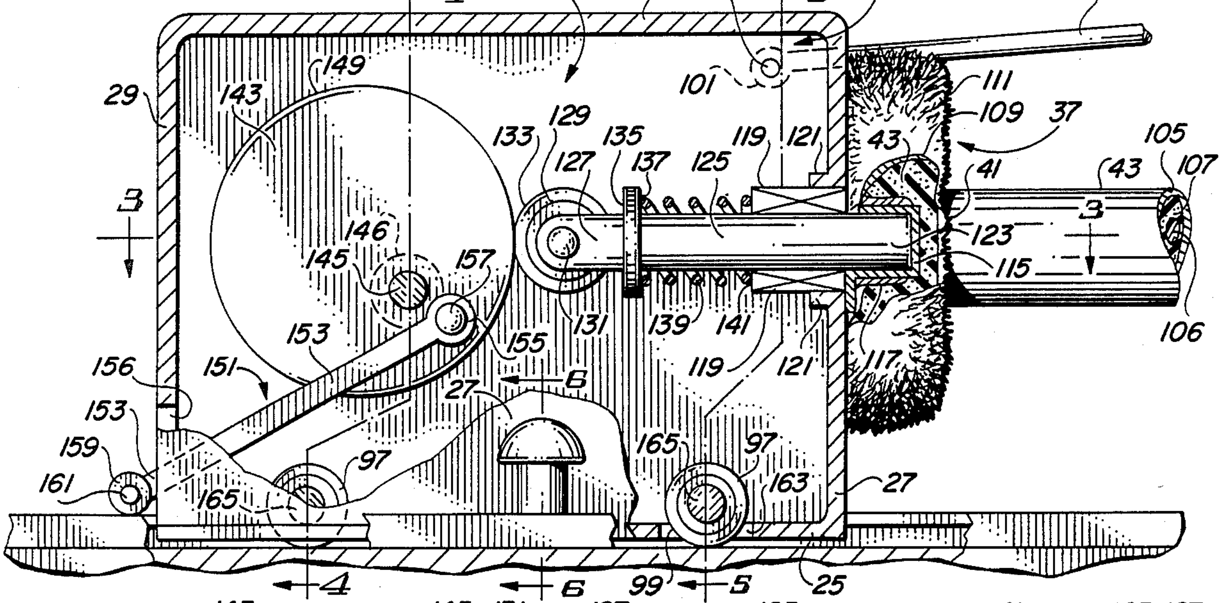
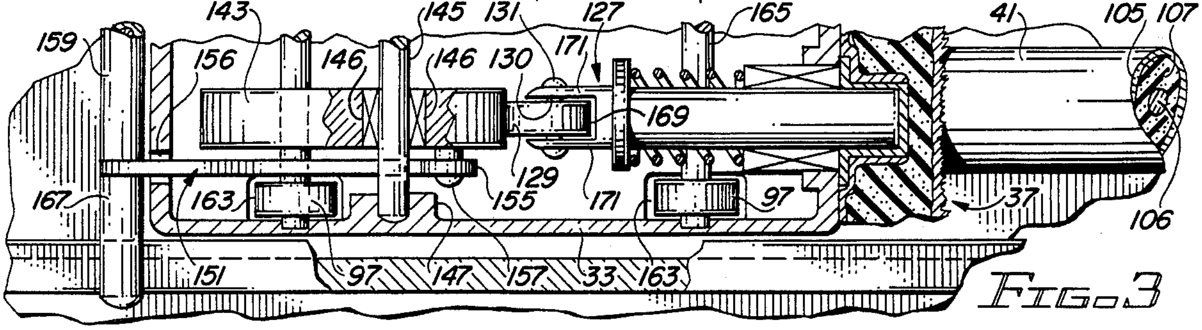
FIG. 3

THERAPEUTIC APPARATUS

BACKGROUND OF THE INVENTION

1. Field of the Invention

This invention relates generally to a therapeutic apparatus, and more particularly to a therapeutic apparatus for relieving tension and sexual frustration in women without sex partners.

2. Description of the Prior Art

There have always been men and women who are or become sexually frigid, impotent, or unable to practice normal sex for one or more reasons. For example, a woman's husband or spouse may be overly obese so as to render sex nearly impossible. Furthermore, diabetics may often become impotent, as do user's of certain medications over long periods of time. Even further, however, since men die a considerable number of years before their wives, the wife is quite often left without her normal or usual sex partner and has nowhere to turn for sexual satisfaction.

Conventional therapeutic devices available in the market place include various types of vibrators and sex sides. Many of these sex aides require the use of another partner, either male or female. Furthermore, many do not provide the true "feel" of a male penis and hence do not result in true sexual gratification, enjoyment, or satisfaction. Many are simply artificial, such as plastic vibrators, and cannot satisfy the true needs of a partnerless woman who wants not only the ultimate climax or orgasm, but also the feeling that she is actually having sex with a partner.

Therefore, a long-felt but unfilled need has existed and continues to exist in the art for a therapeutic apparatus for more closely simulating sexual intercourse, which has the look and feel of a real male penis, and which can be used at any tempo, manner, or degree of gentleness or roughness, as desired by the user.

The present invention solves many of the problems of the prior art while avoiding many of its shortcomings.

BRIEF SUMMARY OF THE INVENTION

It is an object of the present invention to provide a therapeutic apparatus for relieving sexual tension and frustration in women without sex partners.

It is another object of the present invention to provide a therapeutic apparatus which utilizes a continuously erect, yet resiliently pliable, artificial penis for simulated sexual intercourse wherein the penis has both the look and feel of a real male's penis.

It is a further object of the present invention to provide a therapeutic apparatus for simulated sexual intercourse which provides the required degree of gentleness or roughness as desired by the user.

It is still another object to provide a therapeutic apparatus for simulating sexual intercourse which is entirely self-operated by the user.

It is still a further object of the present invention to provide a therapeutic apparatus which provides a rapid cam-operated thrust at the end of each stroke.

It is yet another object of this invention to provide a pad encircling the base of the penis to simulate the look and feel of male pubic hair.

It is yet a further object of the present invention to provide a therapeutic apparatus which can be manually-operated by the user in any number of comfortable positions for achieving sexual gratification by simulated sexual intercourse.

The present invention provides a therapeutic apparatus for relieving sexual frustration, tension, and a lack of "fulfillment" in women, and usually in women without sex partners. A generally rectangular, substantially planar, platform means includes a body portion having a front end, a rear end, and a longitudinal axis. The platform means is dimensioned for placement between the female user's partially spread legs and thighs such that the front end of the body portion of the platform is operatively disposed adjacent the user's exposed vulva. A pair of longitudinal rail members are operatively carried by the top surface of the body portion of the platform and the rails are provided with a continuous inwardly disposed slot in each for engaging a corresponding laterally outwardly extending flange on the bottom of the housing. This prevents motion in any direction except along the path of the tracks or rail means. A manually operable member is provided for selectively moving the housing means reciprocally back and forth along the track means for penetrating and entering the vagina of the user and withdrawing therefrom in the act of simulated sexual intercourse. A penial assembly is operatively mounted proximate the front of the housing means. The assembly includes an elongated, generally cylindrical, resilient tubular member for simulating the look and feel of an erect human male's penis and further including an annular pad of relatively soft material operatively disposed adjacent the front of the housing and about the base of the tubular member for simulating the look and feel of a human male's pubic hair.

These and other objects and advantages of the present invention will become more fully understood after reading the Detailed Description of the Preferred Embodiment, the claims, and the Drawings which are briefly described hereinbelow.

BRIEF DESCRIPTION OF THE DRAWINGS

FIG. 1 shows a perspective view of the therapeutic apparatus of the present invention;

FIG. 2 is a sectional side view of the therapeutic apparatus of FIG. 1 taken along view lines 2—2 thereof;

FIG. 3 is a top sectional view of the apparatus of FIG. 2 taken along view lines 3—3 thereof;

FIG. 6 is a partially exploded view of the apparatus of FIG. 2 taken along view lines 6—6 thereof;

DETAILED DESCRIPTION OF THE PREFERRED EMBODIMENTS

Figure 4:
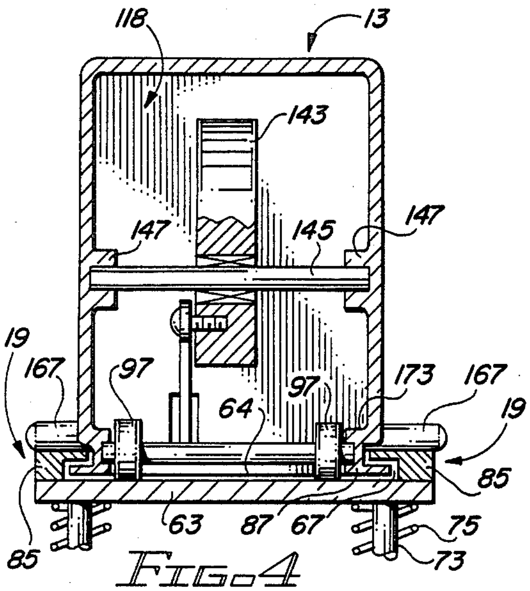
FIG. 4 is a sectional end view of the apparatus of FIG. 2 taken along view lines 4—4 thereof.

FIG. 1 illustrates the therapeutic apparatus 11 of the present invention as including a box-like housing 13, a penial assembly 15, a platform assembly 17, a track or rail assembly 19, and a manually-operated operating device 21.

The box-like housing unit or apparatus 13 includes a top 23, a bottom 25, a front 27, a rear 29, a left side 31, and a right side 33. The housing 13 also includes a trailing stop-engagement member 35, as hereinafter described.

A penial assembly 15 includes a generally circular or annular wool pad 37 and an artificial or simulated male penis 39. The penis 39 includes a base or base portion 41 at the rear end of the elongated shaft 43 and a penetration end, tip, or head 45 of the penis 39 disposed at the front end thereof.

The platform assembly 17 includes a rear platform member or platform panel 47, a center platform member or central panel 49, and a front platform member or front platform panel 51. A hinge member 53, such as a conventional piano hinge, connects the rear panel 47 to the central panel 49, while a second, substantially identical, piano hinge 55 hingedly connects the central panel 49 to the front panel 51. The top surface of each of the panels is designated by reference numeral 57, the bottom platform surfaces are designated by the reference numeral 59, and the platform sides are designated by the reference numeral 61.

The track assembly 19, in the embodiment of FIG. 1, includes a generally planar intermediate web or base portion 63 having a top surface 64. The sides of the base portion 63 connect at the opposite lateral ends to the tracks or rails 65. Disposed laterally inward of the tracks or rails 65 are continuous elongated hollow slots 67 disposed between the top portion of the tracks 65 and the top surface 64 of the base member 63.

Furthermore, a screw or similar externally-threaded member 69 is disposed between the rails 65 and the top surface 57 of the central panel 49. The screws 69 include a screw head portion 71 and an elongated, externally-threaded screw body portion 73 which threadedly engages an aperture (not shown) in the top surface 57 of the central plate or platform member 49. A coiled spring 75 is disposed vertically over the longitudinal screw body 73 with one end being compressed against the lower surface of the rail 65 and the opposite end being compressed against the top surface 57 of the central panel 49 so that the action of the spring 75 upon the screw member 69 is to provide for shock absorption of the housing 13 as it rides along the tracks 65.

Referring briefly to FIG. 6, the slot 67 can be described with reference to the base member 63 and the rails or tracks 65. In FIG. 6, the lower portion of the housing 13 forms the bottom 25. The top surface 64 of the intermediate base 63 is disposed a predetermined distance from the lower surface 25 of the housing 13 due to the contact of the wheels 97 with the top surface 64 of the base 63. The stop member or stop posts 77 is shown as including an internal screw member having a head 89 and an elongated, externally-threaded body portion 91. This member holds or secures the cap of resilient material including the stem or collar portion 83 and the head or mushroom-shaped portion 81 over the threaded member 89, 91 for preventing unnecessary shock when the trailing stop-engaging bar or member 35 comes into contact therewith. Additionally, the trailing contact member will also be coated with a layer of resilient material for further decreasing physical shock when contact is made.

A generally L-shaped track member 85 has one leg portion disposed horizontally with reference to the plane of the top surface 64 of the base 63 and its laterally outward leg disposed vertically with respect thereto. A slot or open recess 67 is formed between the lower surface of the upper leg 85, the inner surface of the vertically downward leg portion of member 85, and the top surface 64 of the base member 63. This elongated, continuous recess or slot 67 enables the flange-like extension 87 at the bottom 25 of the housing 13 to extend a predetermined distance into the slot 67 and be constrained therein since a similar flange on the opposite side engages a similar slot in the opposite track. In this manner, the motion of the housing along the tracks or rails 65 is constrained to back and forth reciprocal movement only to prevent damage should it otherwise jump the track.

In FIG. 1, the manually-operable operating device 21 is shown as including a generally elongated. Longitudinal, intermediate, rod-like portion 83 having a housing-engaging rear end 85 and a forward end shaped in the form of a handle 87 adapted to be gripped by the user to physically and manually operate the therapeutic apparatus 11 of the present invention by moving it toward and away from her vagina while it is constrained within the tracks for repeated insertion and withdrawal for artificially simulating sexual intercourse.

FIG. 2 shows an eyelet 101 at the rear end 85 of the elongated rod-like member 83 and a pin or screw-type member 103 inserted through the aperture of the eyelet 101 to secure the manually-operable rod 83 to the housing 13.

The penial apparatus 15 is further shown as including a generally hard or at least partially rigid plastic inner core member 106 having a relatively thick covering of resilient material forming an outer coating or covering 107 over and about the inner core member 106. A condom, rubber, or prophylactic 105 may then be removably placed on and taken from the resilient foam portion, as desired by the user, to prevent infections and the like so that a new prophylactic would be used each time the apparatus of the present invention is used to prevent infections, irritations, or even disease.

The wool pad or annular pad 37 includes a generally cylindrical disk-like interior of resilient material 113 covered by an outer covering 109 having wool, fur-like or hair-like material 111 on the external surface thereof. A first generally cup-shaped member 115 is provided within an annular support collar 117 which extends radially outwardly as the plastic disk serves as a base or rear surface of the pad 37. An elongated cylindrical rod or shaft has an intermediate portion 125, a rear portion 127, and a front portion 123. The front portion 123 is adapted to be operatively fitted within the hollow interior of the cup-shaped portion 117, while the intermediate portion 125 passes between bearings 119 disposed between the intermediate shaft portion 125 and the collar 121 formed about the aperture containing the bearings 119 and the shaft 125. The front end portion 127 of the shaft includes a bifurcated pair of arms having apertures therethrough, and a pin 131 is fitted through the apertures and through the central aperture of a cam follower wheel 129 whose outer peripheral surface 133 rotates about the lateral axis of the pin member 131. An annular ring or stop collar 135 is provided along the intermediate portion 125 of the shaft adjacent to but disposed a predetermined distance from the rear end 127 thereof. The front surface 137 of the annular collar or ring member 137 serves to abut one end of a coiled spring 139 which is operatively fitted over and around the external periphery of the intermediate shaft portion 125 while the opposite end of the spring 139 is housed abuttedly against the rear surface 141 of the bearings 119. In this manner, the elongated shaft can be moved forward, as hereinafter described, to insert the artificial penis further into the vagina of the user by an extra rapid thrust providing an additional distance of penetration over and above that which can be accounted for by the motion of the housing along the tracks, as hereinafter described.

A cam wheel 143 includes an outer eccentric cam surface 149 and a cam shaft 145 disposed within the cam 143 via bearings 146. A pin 157 passes through an eyelet 155 to fasten one end of a link assembly 151 to the cam 143 while the intermediate portion 153 of the link 151 passes through an aperture 158 in the rear 29 of the housing 13 and encircles a laterally, outwardly-extending stop-engaging member 161 wrapped within a resilient plastic material 159 for shock reduction purposes, as previously described. The end portion 158 of the link 151 is shown as extending through a bottom portion of the aperture or the slot 156, as previously described.

In FIG. 2, the stop member 77 is shown as being mounted on the top surface of one of the rails 65, and a pair of wheels 97 are operatively mounted by axies 165 adjacent the lower portion of the housing 13 for supporting the weight of the housing thereon and for rolling the housing back and forth between the tracks 65 as described. The lower surface portion 99 of the rotating wheels 97 extend through the wheel apertures 93 and ride upon the intermediate rail-connecting base member 63 in the preferred embodiment of the present invention. The wheel axies 185 are mounted for rotation or journalled in collars disposed on the opposite inside bottom portions of the housing 13.

FIG. 3 is a sectional top view of the apparatus of FIG. 2 taken along view lines 3—3 thereof. FIG. 3 shows the outer peripheral surface 133 of the cam follower wheel 129 bearing against and riding on the exterior peripheral eccentric surface 149 of the cam wheel 143. Furthermore, the opposite ends of the axies 165 are shown as being journalled into the side 33, and the lower surfaces 99, not shown, of the wheels 97 are shown as extending through the wheel apertures 163 to contact the riding or rolling surface 163. Furthermore, the link 151 is shown as being connected at one end by pin 157 through the eyelet 155 to the cam 143, while the cam shaft 145 is shown as passing through the bearings 146 before having its opposite ends journalled into collars 147. Lastly, the link member is shown as having a portion passing through the aperture 156 and encircling the stop member-engaging rod or member 35 whose laterally extending portion 167 is shown in FIG. 3. Furthermore, the rigid central core 106 is shown as being disposed centrally along the axis of the cylindrical member 39.

Figure 5:
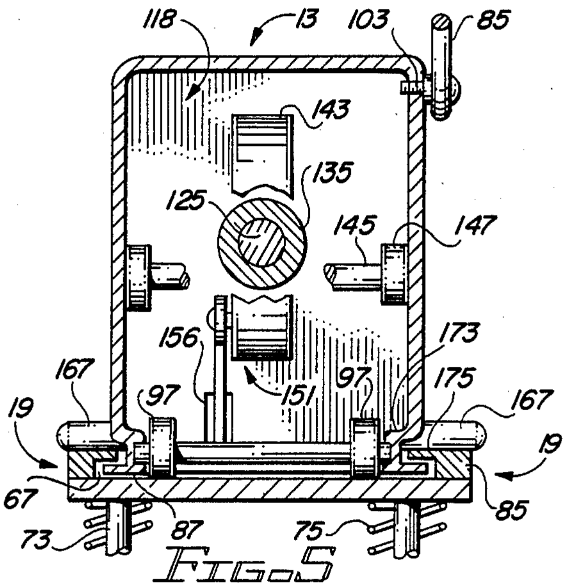
FIG. 5 is a sectional front view of the apparatus of FIG. 2 taken along view lines 5—5 thereof.

FIG. 4 shows the spring members 75 about the members 73 for supporting the base member 63 a predetermined distance above the surface 57 of the central panel 49. This provides shock absorption properties. FIG. 4 shows the relationship of the laterally outwardly-extending flange portions 87 entering the recesses or slots 67 formed by the rails 85 to constrain the motion of the housing 13 to reciprocal motion back and forth motion between the tracks and to no other direction of movement. FIG. 5 shows an opposite end view of the housing 13 and shows the cam follower wheel-driven shaft 125 and the annular spring abutment member 135 which enables the spring for pulling back the penis 39 after it has been thrust inward at the end of each stroke.

FIG. 6, was previously described but also shows a wheel 97 as having its outer peripheral portion 99 disposed or riding upon the upper surface 64 of the base 63 for smooth back and forth motion of the housing 13.

Figure 6A:
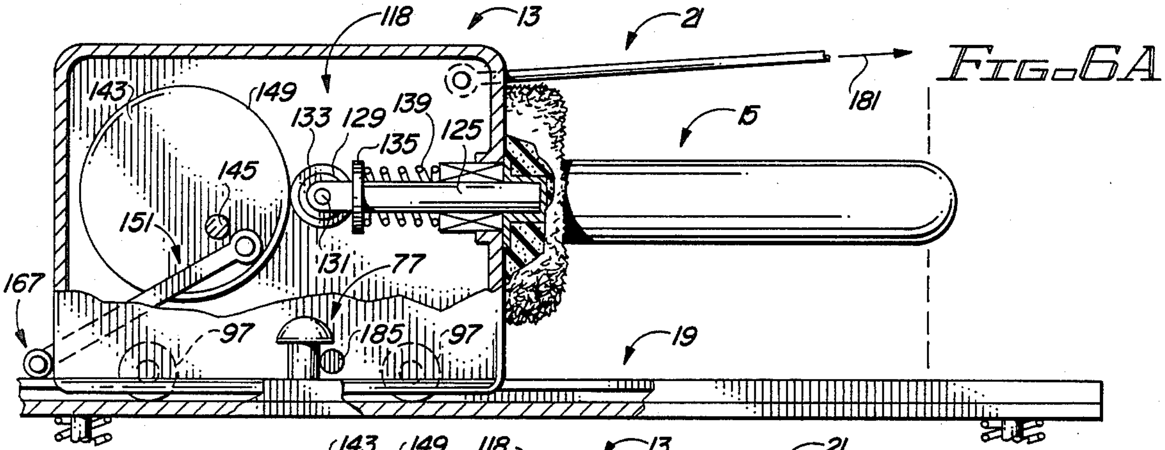
FIG. 6A is a partially sectional, partially perspective view of the apparatus of FIG. 1 at a first predetermined position.
Figure 6B:
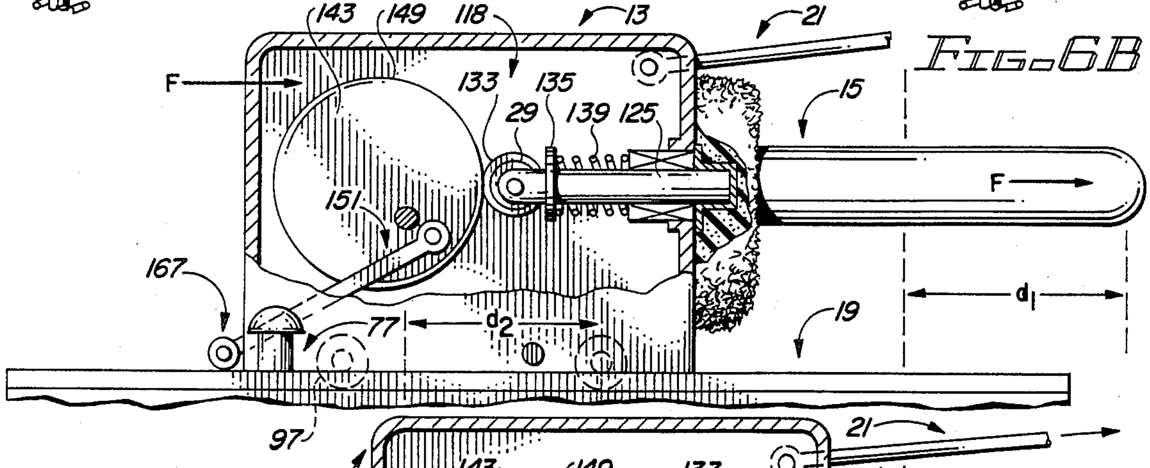
FIG. 6B is a partially sectional, partially perspective view of the apparatus of FIG. 1 in a second predetermined position.
Figure 6C:
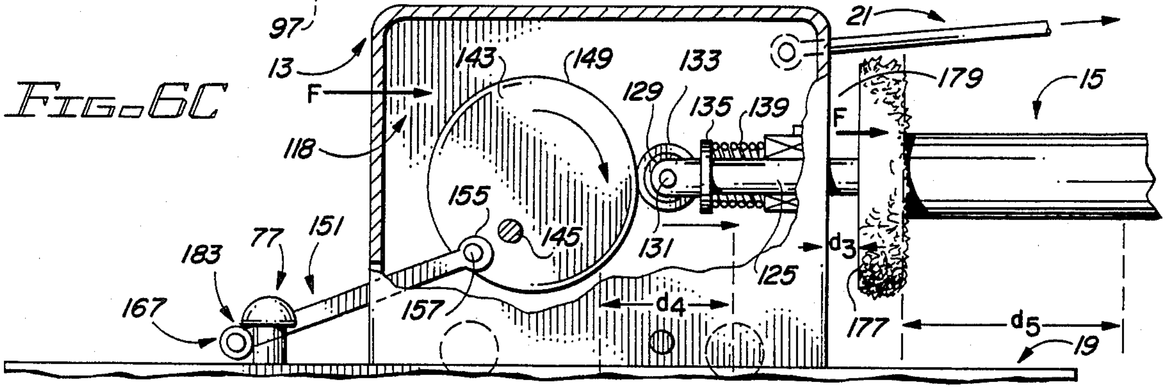
FIG. 6C is a partially sectional, partially perspective view of the apparatus of FIG. 1 in a third predetermined termination position.

FIG. 6A shows the position of the therapeutic apparatus 11 of the present invention at either the end of the return stroke or the very beginning of the insertion stroke since the pin member 185 abuts the forward side of the stop member 77 to prevent any further rearward motion. Assuming that the user then grips the handle 87 at the front end of the elongated rod 83 and pulls the apparatus forward, to the right as shown in FIGS. 6A, 6B, and 6C, the head of the penis 45 and a portion of the elongated shaft 43 will push open the vulve and enter the vagina. The distance moved by the head end of the penis will be equal to the distance traversed by the wheels of the housing 13.

FIG. 6B shows the therapeutic apparatus 11 of the present invention having been pulled forward until the laterally extending stop-engaging member or portion 167 is about to engage or abut the stop member 77. At this point, the distance of movement or penetration of the penis 39 is again equal to the distance traversed by the wheels of the housing 13. However, FIG. 6C shows the forward motion of the housing 13 after the member 167 has engaged the stop member 77 as at point 183 to eventually stop the forward motion at a second predetermined termination position or a final predetermined position with respect to the position of the head of the penis 45.

The depth of penetration after engagement of the member 167 with the stop member 77 is a function of two variables rather than one. The first variable is identical to that previously described in that the shaft 43 of the penis 39 is inserted an additional distance into the vagina which is exactly equal to the distance travelled by the housing 13 from the first predetermined position at which the extension portion 167 first contacts the stop member 77 to the termination position-plus an exta added distance which is provided with a rapid inward thrust adjacent or near the end of the stroke. The additional distance can be given as the distance of the gap 179 between the rear surface of the plastic member 177 on the rear of the pad 37 and the front surface of the front 27 of the housing 13. The distance d3 measured in this gap plus the distance travelled by means from the point of initial engagement with the stop member 77 to the arrival at the termination position, as defined by the length of the link member 121, etc. so that the penis actually thrusts rapidly inward a distance d5 equal to the sum of d3 and d4. Again, since this is done as a quick initial thrust for added satisfaction and stimulation, it provides or results in an additional feeling of naturalness to the sex act.

In operation, after the stop member-engaging portion 167 contacts the stop post or stop member 77, the housing 13 can only move a predetermined distance d4 forward on its wheels until it reaches the termination position. As this occurs, the cam wheel 143 will be rotated by the force applied to the extending ends 167 of the stop member-engaging rod 159, and the cam follower wheel 129 riding on the eccentric surface of the cam 143 will push the rod 125 forward against the bias of the spring member 139 to its maximum point of penetration. The force of the compressed spring 139 will then quickly withdraw a portion of the shaft a distance from its point of maximum penetration in readiness for the rearward movement of the housing 13 under the control of user by means of the operation of the elongated bar 83.

It will be realized that the therapeutic apparatus of the present invention may be used anally on both men and women, as well as vaginally on a female user, from either a position wherein she is reclining on her back or a position wherein she is reclining on her stomach. Furthermore, any number of positions can be enjoyed with the apparatus of the present invention by using a little imagination and practice. Not only does the feel and look of the artificial penis and pad provide a much more life-like simulation of sexual intercourse, but the extra thrust and partial withdrawal at the end of each forward thrust or cycle greatly adds to the natural feeling of the act and greatly adds to the sexual satisfaction. gratification, and stimulation further assisting the user to more rapidly reach a climax or orgasm. Even without the cam-operated and thrust and withdrawal motion, the present invention is still far superior to anything known in the prior art for true stimulation of sexual intercourse. Many psychological as well as physical problems can be alleviated using the present invention as a therapeutic apparatus including, but not limited to, the psychological need for sexual gratification, satisfaction, and a feeling of "completeness" or "wholeness". The present invention provides a true feel and look of both the male penis and the male's pubic hair, and enables the user to operate the apparatus in either a very slow and gentle manner or in a very fast and erratic manner, depending upon the user's particular wants and desires. Furthermore, the artificial penis 39 could be interchangeable with various penis's of other shapes, sizes, curvatures, and diameters, as desired. Still further, the intermediate base 63 connecting the track 65 could eliminated together with the shock absorption springs 75 so that the track 65 could be disposed directly upon the top surface 57 of the intermediate panel 49, if desired.

It will be recognized by those of ordinary skill in the art that various modifications, variations, substitutions, changes, and alterations can be made in the form, structure, detail, and method of operation of the present invention, without departing from the actual spirit and scope of the invention, which is limited only by the appended claims.

What I claim is:

1. A therapeutic apparatus for relieving tension and sexual frustration in women without sex partners comprising:

a generally rectangular, substantially planar, platform means including a body portion having a front end, a rear end, and a longitudinal axis therebetween, said platform means being dimensioned for placement between a female human user's at least partially spread legs and thighs such that the the front end of said body portion is disposed adjacent the user's exposed vulva;

rail means including a pair of longitudinal rails operatively carried by the top surface of said body portion of said platform means, said pair of rails being spaced a predetermined distance apart, being generally parallel to one another and to said longitudinal axis, and extending longitudinally along the body portion between said front and rear ends thereof:

housing means including a rail-engaging, outwardly-extending flange means for operatively engaging said rail means to constrain the movement of said housing means to back and forth reciprocal motion between said pair of rail means;

manually-operable means for selectively moving said housing means reciprocally back and forth along said rail means; and a penial assembly operatively mounted proximate the front of said housing means, said penial assembly including an elongated, generally cylindrical, at least partially resilient tubular member means for simulating the look and feel of an erect human male's penis, said tubular member including an intermediate, elongated body portion, a base, and a penis head, said penial assembly further including an annular pad of relatively soft material means operatively disposed adjacent the front of said housing means and about the base of said tubular member means, said soft material means for simulating the look and feel of said male's pubic hair.

2. The therapeutic apparatus of claim 1 further including wheel means operatively coupled to the base portion of said housing means for carrying the weight of said housing means thereon and for rolling motion along a surface portion of said body portion intermediate said pair of rails.

3. The therapeutic apparatus of claim 1 wherein said rail means includes a pair of laterally displaced rails and an intermediate, continuous, relatively planar base portion interconnecting said pair of rails, a laterally interior portion of each of said pair of rails including means for forming a continuous elongated slot along the length thereof, said slots for operatively engaging the outwardly extending flange means of said housing means for constraining the movement of said housing means to back and forth reciprocal motion between said rail means.

4. The therapeutic apparatus of claim 3 wherein the bottom portion of said housing means includes wheel means for carrying the weight of said housing means thereon and for rolling motion on the upper surface of said intermediate base portion of said rail means for reciprocal back and forth movement therebetween.

5. The therapeutic apparatus of claim 4 wherein said rail means is operatively mounted a predetermined distance away from the plane of the body portion of said platform means on spring means for shock-absorbing purposes.

6. The therapeutic apparatus of claim 1 wherein said elongated, generally cylindrical, at least partially resilient tubular member means includes a central inner core of relatively rigid material for providing the erect state of said tubular member means;

an outer covering of relatively resilient material operatively disposed about said inner core for providing the proper look and feel to said tubular member means.

7. The therapeutic apparatus of claim 6 further including a prophylactic removably disposed over said outer covering of relatively resilient material of said tubular member means.

8. The therapeutic apparatus of claim 1 wherein said housing means includes a substantially hollow interior and operatively housed within said interior are disposed:

a cam shaft;

a cam wheel mounted for eccentric rotation about said cam shaft;

a laterally disposed stop-engaging member adapted to be pulled along behind said housing means;

an apparatus in the rear of said housing means;

a link means having an intermediate body portion, a front end portion and a rear portion, the front end portion of said link means being operatively coupled to a portion of said cam wheel and the opposite rear portion of said link means extending through said housing means aperture for encircling a portion of said lateral stop-engaging member;

cam follower means for operatively engaging the outer peripheral eccentric surface of said cam wheel;

a shaft having one end operatively coupled to said cam follower and the opposite end operatively coupled to the base of said tubular member means;

the top surface of at least one of said pair of rails including a stop member;

said laterally extending stop-engaging member being responsive to contact with said stop member for rotating said cam wheel and lunging said tubular member a predetermined distance forward, said predetermined distance being greater than the distance which said housing means can travel after such contact.

9. The therapeutic apparatus of claim 8 wherein said stop member includes a resilient coating thereon for shock absorption purposes and wherein said laterally-extending stop-engaging member includes at least a partially resilient coating thereon for shock absorption purposes when contacting said stop member.

10. The therapeutic apparatus of claim 1 wherein said manually-operable means for selectively moving said housing means reciprocally back and forth along said rail means includes a generally elongated member having one end operatively coupled to said housing and the opposite end terminating in handle means adapted to be gripped by the user to push and pull the housing means reciprocally away and toward her vulva such that substantially the entire length of said tubular member penetrates the user's vagina and can produce an orgasm for alleviating tension and sexual frustration.

11. A therapeutic sex machine for use by sexually frustrated human female users without sex partners comprising:

a box-like housing means having a front end, a rear end, a top, a bottom, and a pair of opposite sides enclosing a substantially hollow interior;

an artificial penis having a relatively stiff elongated tubular means for simulating the look and feel of an erect human male penis, said tubular means including a base at the rear end thereof and a head at the front end thereof, said base being operatively mounted to the front end of said housing means;

platform means including a generally planar intermediate body portion having a top surface, a rear end, a front end, and a longitudinal axis extending along the longitudinal axis of said body portion between the front and rear ends thereof, said platform means being dimensioned for placement between the at least partially spread legs and thighs of said user such that the front end is disposed immediately adjacent to the user's exposed vulva and proximate the user's vagina;

longitudinal path means operatively carried by the top surface of said intermediate body portion and extending substantially parallel to the longitudinal axis thereof between said front and said rear end;

means operatively carried by the bottom of said housing means for operatively engagin said path means and enabling said housing means to be easily moved reciprocally back and forth along said path means while simultaneously restricting said housing means from movement in any other direction;

manually-operable means operatively coupled to said housing means for enabling the user to reciprocally move said housing means back and forth along said path means for successively inserting and removing said artificial penis into and out of the user's vagina for imparting sexual stimulation and satisfaction to said user;

said path means including at least a first and a second predetermined location therealong, said housing means being responsive to having been manually moved forward to a first predetermined location for inserting the head of said elongated tubular means and the intermediate shaft portion thereof a first predetermined distance into said user's vagina, the first predetermined distance being equal to the distance said housing means moves along said shaft means from start of penetration until reaching said first predetermined distance therein;

said path means including means for stopping the forward movement of said housing means at a second predetermined termination location at which said artificial penis has been inserted a second additional predetermined distance into the user's vagina, said second predetermined distance being at least equal to the distance said housing means has moved forward from said first predetermined location to said termination location; and means operatively disposed within the hollow interior of said housing means and responsive to the movement of said housing means between said first predetermined location and said termination location for relatively rapidly thrusting said artificial penis a third additional distance into and then at least a portion of the way out of the user's vagina for additional sex stimulation and gratification.

12. The therapeutic sex machine of claim 11 wherein said artificial penis includes a generally rigid core member for imparting stiffness thereto; and an outer layer of resilient means operatively disposed about said core member for providing the proper feel and appearance to said artificial penis.

13. The therapeutic sex machine of claim 12 further including a prophylactic operatively and removably disposed over the outer layer of resilient means for enabling the user to replace said prophylactic with each use of said sex machine for preventing at least one of infections, irritations, and diseases.

14. The therapeutic sex machine of claim 11 wherein said platform means includes a front panel, a rear panel, and an intermediate panel corresponding to said intermediate body portion, said front panel being adapted to be disposed under the user's buttocks, said center panel being adapted to be disposed between and under the user's at least partially spread legs and thighs; and the rear panel being adapted to be operatively disposed under the user's feet.

15. The therapeutic sex machine of claim 11 wherein said path means includes a pair of substantially parallel rails operatively disposed on the top surface of the intermediate body portion of said platform means, the bottom of said housing means includes a pair of longitudinal bottom sides having outwardly extending flange means thereon, said pair of tracks including inwardly facing slots for operatively engaging the flange means of said housing means to prevent any type of movement except for reciprocal back and forth movement along said pair of tracks.

16. The therapeutic sex machine of claim 15 wherein the lower portion of said housing means includes a plurality of wheels adapted to carry the weight of said housing means and to ride upon the surface of the intermediate body portion of said platform means.

17. The therapeutic sex machine of claim 11 wherein said path means includes a pair of longitudinally extending substantially parallel tracks each having a longitudinal inwardly disposed continuous slot formed therein;

a central panel operatively connecting said pair of tracks for forming said path means therebetween;

the lower portion of said housing means including laterally extending flange means and wherein said pair of rails include inwardly disposed continuous slots therein, said flange means being operatively disposed within said slots for restricting the motion of said housing means to reciprocal back and forth motion along said pair of tracks.

18. The therapeutic sex machine of claim 17 wherein the central panel connecting said pair of tracks is disposed a predetermined distance above the upper surface of said intermediate body portion of said platform means by spring means for shock absorbing purposes.

19. The therapeutic sex machine of claim 18 wherein the lower portion of said housing means includes a plurality of wheel means for carrying the weight of said housing means and for rolling along the upper surface of said base between said pair of tracks.

20. The therapeutic sex machine of claim 11 further including a stop member operatively disposed adjacent said path means, mechanical means operatively housed within the hollow interior of said housing means and including:

a stop member operatively disposed adjacent said path means;

means operatively extending from the interior of said housing for abutting said stop member at a first predetermined location;

means responsive to the continued forward motion of said housing from said first predetermined position to a termination of motion position for inserting said artificial penis a distance equal to the distance to the termination position minus the first position therein and further including means responsive to said continued motion before termination for thrusting the shaft forward rapidly into the vagina and then pulling it rapidly back for increased sexual stimulation, gratification and excitement.

* * * * *